United States Patent [19]
Kameswaran

[11] Patent Number: 5,945,538
[45] Date of Patent: Aug. 31, 1999

[54] AMMONIUM OXAZOLE AND AMINO OXAZOLIUM INTERMEDIATES, METHODS FOR THE PREPARATION THEREOF AND THE USE THEREFOR IN THE MANUFACTURE OF INSECTICIDAL ARYLPYRROLES

[75] Inventor: Venkataraman Kameswaran, Princeton Junction, N.J.

[73] Assignee: American Cyanamid Company, Madison, N.J.

[21] Appl. No.: 08/883,772

[22] Filed: Jun. 27, 1997

Related U.S. Application Data

[60] Provisional application No. 60/020,836, Jun. 28, 1996.

[51] Int. Cl.$^6$ .................................................. C07D 263/42
[52] U.S. Cl. ................................................... 548/233
[58] Field of Search ............................................ 548/233

[56] References Cited

U.S. PATENT DOCUMENTS

| | | | |
|---|---|---|---|
| 3,290,326 | 12/1966 | Hoffer et al. | 548/233 |
| 4,150,143 | 4/1979 | Nevile et al. | 548/233 |
| 4,632,930 | 12/1986 | Carini et al. | 548/235 |
| 5,000,775 | 3/1991 | Grabiar | 548/239 |
| 5,010,098 | 4/1991 | Brown et al. | 514/426 |
| 5,030,735 | 7/1991 | Addor et al. | 548/231 |
| 5,145,986 | 9/1992 | Kameswaran | 548/531 |
| 5,380,738 | 1/1995 | Norman et al. | 548/235 |
| 5,426,225 | 6/1995 | Kameswaran | 564/212 |
| 5,446,170 | 8/1995 | Kameswaran | 548/517 |
| 5,449,789 | 9/1995 | Kameswaran | 548/561 |
| 5,574,175 | 11/1996 | Kameswaran | 548/517 |
| 5,631,379 | 5/1997 | Kameswaran | 548/233 |
| 5,659,046 | 8/1997 | Kameswaran | 548/228 |
| 5,750,726 | 5/1998 | Kameswaran | 548/561 |
| 5,777,132 | 7/1998 | Kameswaran | 548/561 |

OTHER PUBLICATIONS

McEwen, et al., *Synthetic Uses of Open–Chain Analogues of Reissert Compounds*, Journal of Organic Chemistry, 1980, 45, pp. 1301–1308.

McEwen, e t al., *1,3–Dipolar Addition Reactions of Reissert Compounds*, Journal of the American Chemical Society, 1971, 93:18, pp. 4479–4484.

Chemical Abstracts, vol. 78, No. 7, Feb. 19, 1973 Columbus, Ohio, US; abstract No. 43335r,.

Poupaert J. et al..: "N–acyl–.alpha.–aminonitriles in the Pinner reaction" p. 478; column 2; XP002044525 & Syntheses, No. 11, 1972 pp. 622–624,.

*Primary Examiner*—Donald G. Daus
*Attorney, Agent, or Firm*—Timothy J. Babcock

[57] ABSTRACT

There are provided ammonium oxazole intermediates of formula I and amino oxazolium intermediates of formula II, useful in the manufacture of insecticidal arylpyrrole compounds.

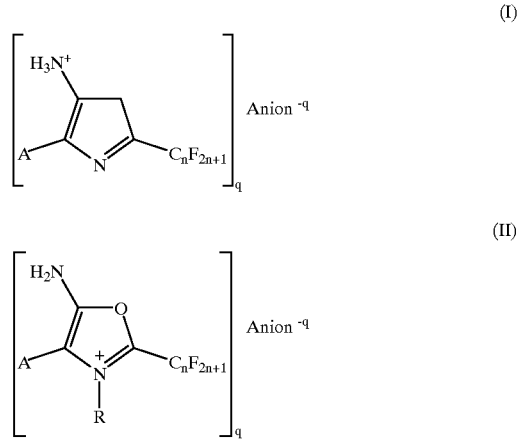

14 Claims, No Drawings

AMMONIUM OXAZOLE AND AMINO OXAZOLIUM INTERMEDIATES, METHODS FOR THE PREPARATION THEREOF AND THE USE THEREFOR IN THE MANUFACTURE OF INSECTICIDAL ARYLPYRROLES

This application claims priority from copending provisional application Ser. No. 60/020,836 filed on Jun. 28, 1996.

BACKGROUND OF THE INVENTION

Arylpyrrole carbonitrile compounds are highly effective insecticidal, acaricidal and nematocidal agents with a unique mode of action and a broad spectrum of activity. In particular, 2-aryl-5-(trifluoromethyl)pyrrole-3-carbonitrile compounds demonstrate effective control across a wide array of pests and can control resistant pests such as pyrethroid-, organophosphate-, cyclodiene-, organochlorine-, organotin-, carbamate-, and benzophenyl-urea-resistant biotypes of Helicoverpa/Heliothis spp., Spodoptera spp., Trichoplusia spp., Pseudoplusia spp. and Tetranychus spp. Because there is no apparent cross-resistance, 2-aryl-5-(trifluoromethyl)pyrrole-3-carbonitrile compounds and their derivatives have potential for use in resistance management programs. Further, said pyrroles have little effect on beneficial species making them excellent candidates for integrated pest management programs, as well. These programs are essential in today's crop production.

Therefore, methods to prepare said pyrroles and intermediates to facilitate their manufacture are of great use. Among the present methods to prepare 2-aryl-5-(trifluoromethyl)pyrrole-3-carbonitrile on a manufacturing scale are the 1,3-dipolar cycloaddition of 3-oxazolin-5-one with 2-chloroacrylonitrile (U.S. Pat. No. 5,030,735) and the cycloaddition reaction of the appropriate oxazole amine derivatives with 2-chloroacrylonitrile or 2,3-dichloropropionitrile (U.S. Pat. No. 5,446,170).

Also known is the 1,3-dipolar cycloaddition of the mesionic intermediate product of the acid catalyzed cyclization of a Reissert compound with a suitable alkyne to give an N-substituted pyrrole product as described by W. M. McEwen, et al, Journal of Organic Chemistry, 1980, 45, 1301–1308. However these mesionic intermediates undergo 1,4-cycloaddition reactions with ethylenic dieneophiles to give an aroylpyrrole derivative and, as such, are not useful as insecticidal arylpyrrole precursors.

Therefore, it is an object of this invention to provide a source of important intermediate ammonium oxazole and amino oxazolium compounds useful in the manufacture of arylpyrrole pesticidal agents.

It is another object of this invention to provide a method to prepare said intermediate compounds.

It is an advantage of this invention that said intermediates may be utilized in a manufacturing process which produces a formula I arylpyrrole precursor capable of being converted to a wide variety of highly effective insecticidal, acaricidal and nematocidal agents.

It is a feature of this invention that said process provides a regiospecific product. These and other features and objects of the invention will become more apparent from the detailed description set forth hereinbelow.

SUMMARY OF THE INVENTION

The present invention provides an ammonium oxazole intermediate of formula I,

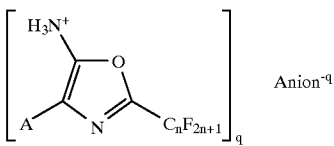

(I)

wherein n is an integer of 1, 2, 3, 4, 5, 6, 7 or 8;
q is an integer of 1, 2, or 3;

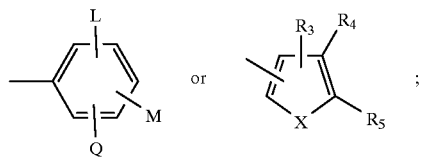

A is
L is hydrogen or halogen;
M and Q are each independently hydrogen, halogen, CN, $NO_2$, $C_1$–$C_4$alkyl, $C_1$–$C_4$haloalkyl, $C_1$–$C_4$alkoxy, $C_1$–$C_4$halo-alkoxy, $C_1$–$C_4$alkylthio, $C_1$–$C_4$alkylsulfinyl or when M and Q are on adjacent positions they may be taken together with the carbon atoms to which they are attached to form a ring in which MQ represents the structure
—$OCH_2O$—, —$OCF_2O$— or —CH=CH—CH=CH—;
$R_1$ and $R_2$ are each independently $C_1$–$C_4$alkyl;
$R_3$, $R_4$, and $R_5$ are each independently hydrogen, halogen, $NO_2$, CHO or $R_4$ and $R_5$ may be taken together with the atoms to which they are attached to form a ring in which $R_4R_5$ is represented by the structure

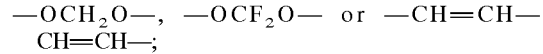

$R_6$, $R_7$, $R_8$ and $R_9$ are each independently hydrogen, halogen, CN or $NO_2$;
X is O or S; and
$Anion^{-q}$ is a proton acceptor having a negative q charge; or
the tautomers thereof.

The present invention also provides an oxazolium intermediate of formula II, or the tautomers thereof,

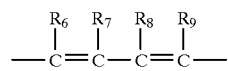

(II)

wherein n, q, A and $Anion^{-q}$ is as described hereinabove for formula I and R is $C_1$–$C_6$alkyl optionally substituted with one $C_1$–$C_4$alkoxy or phenyl group.

3

Further provided are methods for the preparation of the compounds of formula I and formula II and their use in the manufacture of insecticidal, acaricidal and nematocidal arylpyrrole compounds.

DETAILED DESCRIPTION OF THE INVENTION

Processes, to be useful on a manufacturing scale, preferentially contain key intermediate compounds which may be obtained in high to quantitative yield, which are stable either upon isolation or in situ, which may be produced from simple or readily available starting materials and which may be readily converted to the desired end-product of manufacture in a minimum of reaction steps, in optimum yield and purity and, if applicable, regio- or stereospecifically.

It has now been found that 5-ammonium oxazole intermediates of formula I and 5-amino oxazolium intermediates of formula II and tautomers thereof are effective intermediates in the manufacture of 2-aryl-5-(perfluoroalkyl)pyrrole-3-carbonitrile insecticidal, acaricidal and nematocidal agents.

The ammonium oxazole and amino oxazolium compounds of the invention have the structure of formula I and formula II, respectively

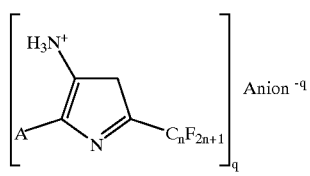
(I)

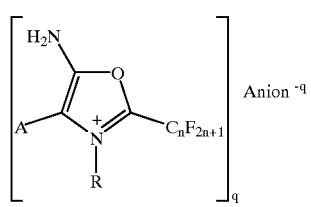
(II)

wherein n is an integer of 1, 2, 3, 4, 5, 6, 7 or 8;
q is an integer of 1, 2, or 3;

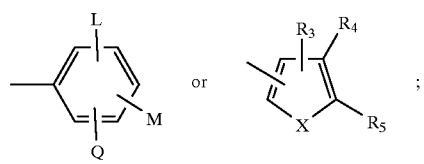

A is
L is hydrogen or halogen;
R is $C_1$–$C_6$alkyl optionally substituted with one alkoxy or phenyl group;
M and Q are each independently hydrogen, halogen, CN, $NO_2$, $C_1$–$C_4$alkyl, $C_1$–$C_4$haloalkyl, $C_1$–$C_4$alkoxy, $C_1$–$C_4$haloalkoxy, $C_1$–$C_4$alkylthio, $C_1$–$C_4$alkylsulfinyl or when M and Q are on adjacent positions they may be taken together with the carbon atoms to which they are attached to form a ring in which MQ represents the structure

4

—$OCH_2O$—, —$OCF_2O$— or —CH=CH—CH=CH—;
$R_1$ and $R_2$ are each independently $C_1$–$C_4$alkyl;
$R_3$, $R_4$, and $R_5$ are each independently hydrogen, halogen, $NO_2$, CHO or $R_4$ and $R_5$ may be taken together with the atoms to which they are attached to form a ring in which $R_4R_5$ is represented by the structure

$R_6$, $R_7$, $R_8$ and $R_9$ are each independently hydrogen, halogen, CN or $NO_2$;
X is O or S; and
Anion$^{-q}$ is a proton acceptor having a negative q charge; or
the tautomers thereof.

The term halogen as used in the specification and claims designates Cl, Br, F or I and the term haloalkyl embraces any alkyl group of $\chi$ carbon atoms which may contain from 1 to $2\chi+1$ halogen atoms which may be the same or different.

The 5-ammonium oxazole intermediate of formula I and the 5-amino oxazolium intermediate of formula II may be represented by their respective tautomeric structures Ia and IIa. Said tautomers are shown below wherein n, q, A, R and Anion$^{-q}$ are as described hereinabove.

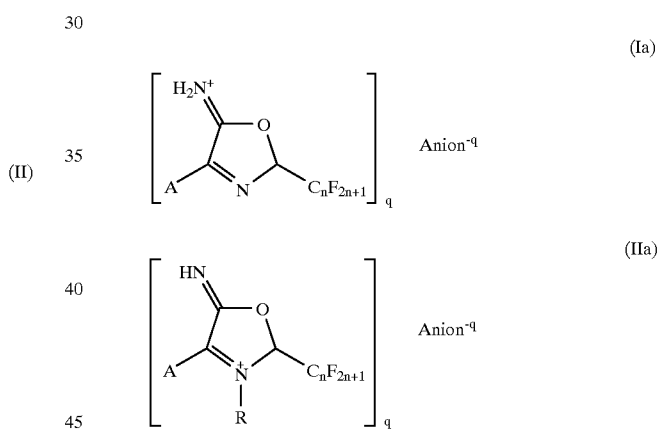

The formula I and formula II compounds of the invention are preferably those compounds wherein q is 1 or 2, with q=1 being especially preferred. Formula I compounds include but are not limited to 5-amino-4-(p-chlorophenyl)-2-(trifluoromethyl)oxazole, methanesulfonic acid salt;

5-amino-4-(p-chlorophenyl)-2-(trifluoromethyl)oxazole, p-toluenesulfonic acid salt;

5-amino-4-(3,5-dichlorophenyl)-2-(trifluoromethyl) oxazole, trifluoromethanesulfonic acid salt;

5-amino-4-(3,5-dichlorophenyl)-2-(trifluoromethyl) oxazole, methanesulfonic acid salt;

5-amino-4-[p-(α,α,α-trifluoro)tolyl]-2-(trifluoromethyl) oxazole, p-toluenesulfonic acid salt;

5-amino-4-(3,4,5-trichlorophenyl)-2-(trifluoromethyl) oxazole, p-toluenesulfonic acid salt;

5-amino-4-[p-(trifluoromethoxy)phenyl]-2-(trifluoromethyl)oxazole, trifluoromethanesulfonic acid salt; or 5-amino-4-[2-(3,4,5-trichloro)thienyl]-2-(trifluoromethyl)oxazole, methanesulfonic acid salt.

The formula II compounds of the invention include but are not limited to 5-amino-4-(p-chlorophenyl)-3-methyl-2-(trifluoromethyl)oxazolium tetrafluoroborate;

5-amino-4-(p-bromophenyl)-3-methyl-2-(trifluoromethyl)oxazolium methanesulfonate;

5-amino-4-(3,5-dichlorophenyl)-3-benzyl-2-(trifluoromethyl)oxazolium p-chlorotoluenesulfonate;

5-amino-4-(3,4,5-trichlorophenyl)-3-isopropyl-2-(trifluoromethyl)oxazolium tetrafluoroborate;

5-amino-4-(p-chlorophenyl)-3-methyl-2-(trifluoromethyl)oxazolium bisulfate;

5-amino-4-[(α,α,α-trifluoro)tolyl]-3-benzyl-2-(trifluoromethyl)oxazolium p-chlorotoluenesulfonate;

5-amino-4-[p-(trifluoromethoxy)phenyl]-3-ethyl-2-(trifluoromethyl)oxazolium tetrafluoroborate; or 5-amino-4-[2-(3,4,5-trichloro)thienyl]-2-(trifluoromethyl)oxazolium methanesulfonate.

Advantageously, the 5-ammonium oxazole intermediates of formula I or the 5-amino oxazolium intermediates of formula II, may be obtained by cyclizing a formula III amide nitrile in the presence of an acid and a solvent under essentially anhydrous conditions. The reaction is shown in flow diagram I wherein q is 1, R' is hydrogen or R and n, A, R and Anion⁻ are as described hereinabove.

Flow Diagram I

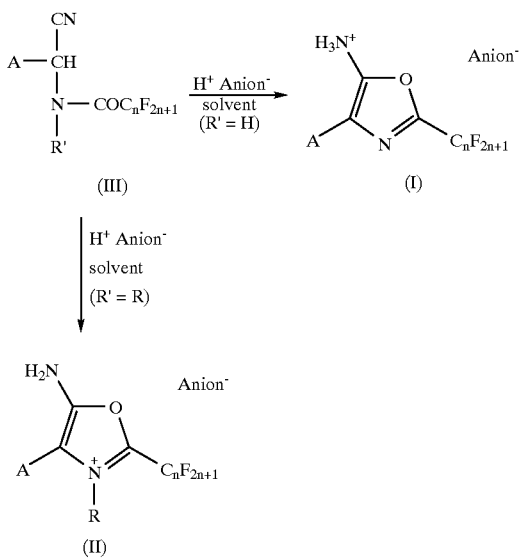

The formula I and formula II intermediates may be isolated by conventional means such as filtration or chromatographic separation and serve as an expedient source of a key intermediate for insecticidal pyrrole manufacture or for future derivatization.

Solvents suitable for use in the above reaction are those organic solvents capable of sustaining essentially anhydrous conditions and partial or complete dissolution of the amide nitrile compound of formula III. Said solvents include: aromatic hydrocarbons such as benzene, xylene, toluene and the like, preferably toluene; chlorinated aromatic hydrocarbons such as chlorobenzene; carboxylic acid amides such as dimethylformamide, N-methylpyrrolidone, and the like, preferably dimethylformamide; nitriles such as acetonitrile, propionitrile, and the like; alcohols such as isopropanol, t-butanol, sec-butanol, and the like, preferably t-butanol. These solvents may be used alone or in combination of two or more.

Acids suitable for use in the formation of the compounds of the invention are any acids capable of relative dehydration. Among the suitable acids are sulfuric acid, methanesulfonic acid, trifluoromethane sulfonic acid, p-toluenesulfonic acid, phosphoric acid, tetrafluoroboric acid, tetrafluoroboric acid complexes, and the like. Boron trifluoride complexes such as boron trifluoride acetic acid, boron trifluoride dihydrate, and the like are also suitable acids.

The formula III amide nitrile compounds wherein R' is hydrogen and their preparation are described in U.S. Pat. No. 5,426,225. Formula III amide nitrile compounds wherein R' is R may be obtained via the perfluoroacylation of the appropriate amino nitrile of formula IV. The formula IV aminonitriles are correspondingly readily obtained from their available benzaldehyde, furfurylaldehyde or thienylmethylaldehyde precursors via the well-known Strecker reaction. The reaction sequence is shown in Flow Diagram II wherein n, A and R are as described hereinabove for formulas I and II, m is an integer of 1 or 2, $X_1$ is Cl, $OR_{10}$ or O and $R_{10}$ is hydrogen or $C_1$–$C_6$alkyl with the proviso that when $X_1$ is O, then m must be 2 and when $X_1$ is Cl or $OR_{10}$, then m must be 1.

Flow Diagram II

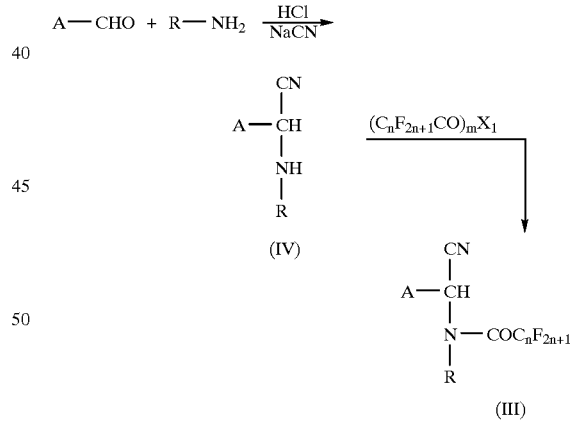

Advantageously, the formula I and II intermediates may be converted to 2-aryl-5-perfluoroalkylpyrroles of formula IV by the 1,3-dipolar cycloaddition of at least one molar equivalent of a dieneophile of formula V in the presence of a solvent and essentially in the absence of water. The conversion is illustrated in Flow Diagram III wherein n, A and R are described hereinabove and q is 1, W is CN, $NO_2$, $COOR_1$, or $COR_2$; $R_1$ and $R_2$ are each independently $C_1$–$C_4$alkyl; and Y is H, Cl or Br with the proviso that when the intermediate compound is formula I, then Y must be Cl or Br.

Flow Diagram III

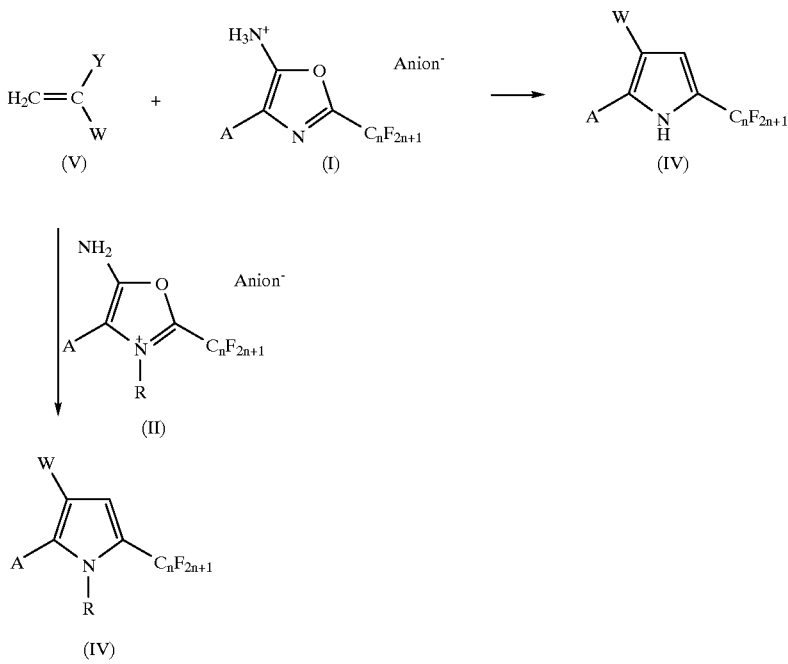

Solvents suitable for use in the above reaction are those organic solvents capable of sustaining essentially anhydrous conditions and partial or complete dissolution of the amide nitrile compound of formula III. To the extent water is present, lower product yield and decreased purity is expected. Said solvents include: aromatic hydrocarbons such as benzene, xylene, toluene and the like, preferably toluene; chlorinated aromatic hydrocarbons such as chlorobenzene; carboxylic acid amides such as dimethylformamide, N-methylpyrrolidone, and the like, preferably dimethylformamide; nitriles such as acetonitrile, propionitrile, and the like; alcohols such as isopropanol, t-butanol, sec-butanol, and the like, preferably t-butanol. These solvents may be used alone or in combination of two or more.

In order to provide a more clear understanding of the invention, the following examples are set forth below. These examples are merely illustrative and are not to be understood to limit the scope or underlying principles of the invention in any way. Indeed, various modifications of the invention, in addition to those shown and described herein, will become apparent to those skilled in the art from the following examples and the foregoing description. Such modifications are also intended to fall within the scope of the appended claims.

The terms $^1$H NMR, $^{13}$C NMR and $^{19}$F NMR designate proton, carbon 13 and fluorine 19 nuclear magnetic resonance, respectively. The term HPLC designates high performance liquid chromatography.

EXAMPLE 1

Preparation of N-Isopropylamino(p-chlorophenyl) aceto-nitrile

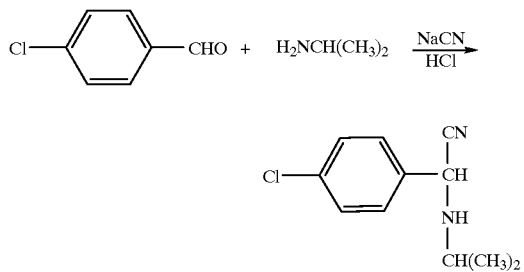

Isopropylamine (88.7 g, 1.5 mol) is added to an aqueous solution of concentrated hydrochloric acid (125 mL, 1.5 mL) in water at 25°–30° C. The resultant mixture is treated sequentially with a solution of sodium cyanide (53.9 g, 1.1 mol) in water and methylene chloride at 30° C., warmed to 35° C., treated with a solution of p-chlorobenz-aldehyde (140.6 g, 1 mol) in methylene chloride over a 15–25 minute period, allowed to warm, held for 3 hours at 45° C. and cooled to room temperature. The phases are separated and the organic phase is washed with water and concentrated in vacuo to give a residue. The residue is crystallized from heptane to give the title product as a pale yellow crystalline solid, 190.3 g (91.2% yield), mp 72.0–73.0° C., identified by $^1$H and $^{13}$C NMR analyses.

EXAMPLE 2

Preparation of N-(p-chloro-α-cyanobenzyl)-2,2,2-trifluoro-N-isopropylacetamide

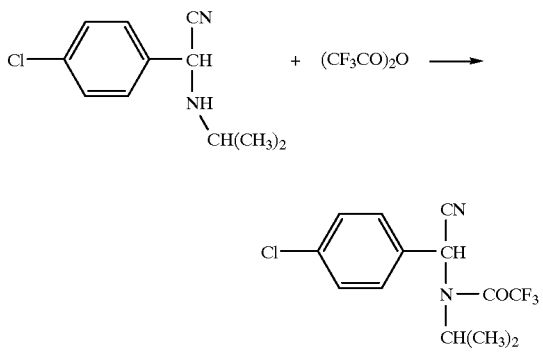

A slurry of N-isopropylamino(p-chlorophenyl)acetonitrile (25.0 g, 0.12 mol) in trifluoroacetic anhydride is gently heated at reflux temperature for 20 hours and concentrated in vacuo to give an oil residue. The oil is crystallized from toluene/heptane to give the title product as a white solid, 26.5 g (72.4% yield) mp 78.5–79.5° C., identified by $^1$H, $^{13}$C and $^{19}$F NMR analyses.

EXAMPLE 3

Preparation of N-Benzyl-N-(p-chloro-α-cyanobenzyl)-2,2,2-trifluoroacetamide

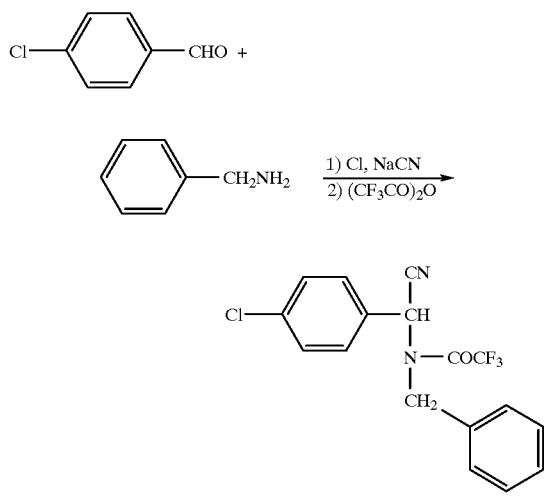

Aqueous hydrochloric acid (62.5 mL of 12 N, 0.75 mol) in water (100 mL) is treated with benzylamine (80.4 g, 0.75 mol) at <20° C., then treated sequentially with a solution of sodium cyanide (27.0 g, 0.55 mol) in water and methylene chloride, warmed to 35° C., treated with a solution of p-chlorobenzaldehyde (70.3 g, 0.5 mol) in methylene chloride, allowed to warm to 50° C., and held at 45° C. for 3.5 hours. The phases are separated and the organic phase is washed with water and concentrated to a syrup residue. The residue is dissolved in toluene and ethyl acetate, treated with trifluoroacetic anhydride (105.0 g, 0.5 mol) at 20°–30° C. over a 30 minute period and diluted with heptane. The resultant white fluffy solid precipitate is filtered and dried to give the title product, 119.8 g (70.7% yield), mp 131–132° C., identified by $^1$H, $^{13}$C and $^{19}$F NMR analyses.

EXAMPLE 4

Preparation of 5-Amino-2-(p-chlorophenyl)-2-(trifluoromethyl)oxazole, trifluoromethanesulfonic acid salt

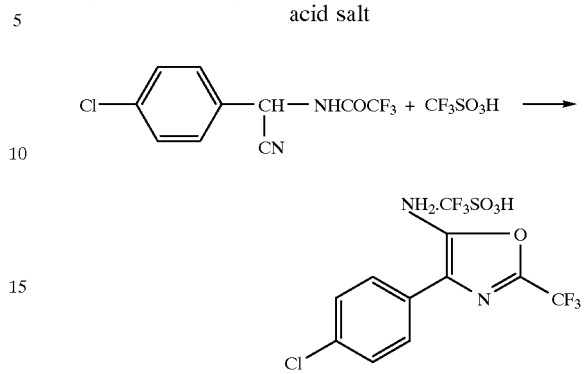

A solution of N-(p-chloro-α-cyanobenzyl)-2,2,2-trifluoroacetamide (21.0 g, 0.08 mol) in ether is treated at room temperature with trifluoromethanesulfonic acid (24.0 g, 0.16 mol) under a nitrogen atmosphere. The ether is slowly evaporated over an 18 hour period to give a pasty solid residue. The residue is treated with ether and filtered and the filtercake is dried to give a yellow solid, 26.7 g (81% yield). A small amount of the solid is recrystallized from ethyl acetate to give the title product, mp 147–150° C. (dec.), identified by $^1$H and $^{19}$F NMR and mass spectral analyses.

EXAMPLE 5

Preparation of 5-Amino-2-(p-chlorophenyl)-2-(trifluoromethyl)oxazole, p-toluenesulfonic acid salt

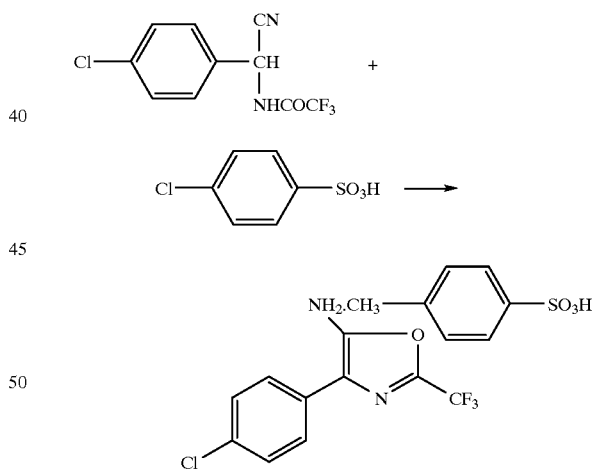

A slurry of p-toluenesulfonic acid monohydrate (16.7 g, 0.088 mol) in toluene is azeotropically distilled using a Dean-Stark trap to obtain anhydrous acid. The resultant dry toluene solution is cooled, treated with N-(p-chloro-α-cyanobenzyl)-2,2,2-trifluoroacetamide (21.0 g, 0.08 mol), heated at 100° C. for 18 hours, cooled and diluted with ether. The resulting mixture is filtered and the filtercake is crystallized from toluene to give a yellow solid 11.0 g (29% yield). A small portion is recrystallized from toluene to give the title product as white needles, mp 164°–165° C., identified by HPLC, $^1$H and $^{19}$F NMR and mass spectral analyses.

EXAMPLE 6

Preparation of (p-Chlorophenyl)-5-(trifluoromethyl) pyrrole-3-carbonitrile

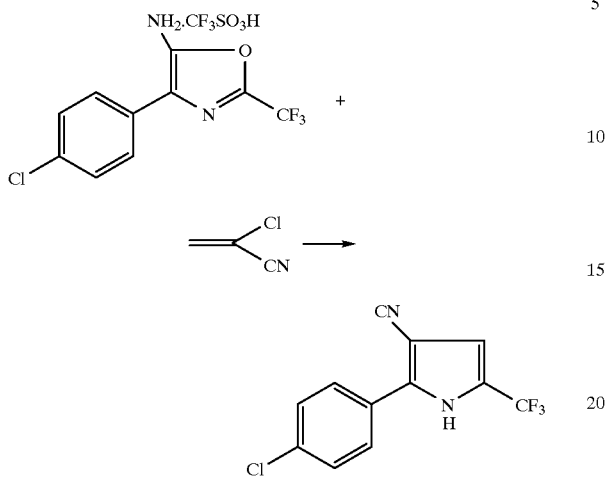

A solution of 5-amino-4-(p-chlorophenyl)-2-(trifluoromethyl)oxazole, triflate salt (16.5 g, 0.04 mol) in dimethylformamide is treated at 10° C. with 2-chloroacrylonitrile (5.25 g, 0.06 mol) under a nitrogen atmosphere, warmed to room temperature, held at room temperature for 4 hours, and treated with a mixture of ethyl acetate and water. The phases are separated and the organic phase is washed with water and concentrated to give a wet solid residue. Flash column chromatography on silica gel, packed with 15% ethyl acetate in heptane and eluted with 20% ethyl acetate in heptane of the residue gives, on crystallization from ethyl acetate/heptane, the title product as a pale yellow solid, 7.1 g (65% yield), mp 238.0°–241.0° C., identified by NMR analysis.

EXAMPLE 7

Preparation of 5-Amino-4-(p-chlorophenyl)-3-methyl-2-(trifluoromethyl)-oxazolium fluoroborate

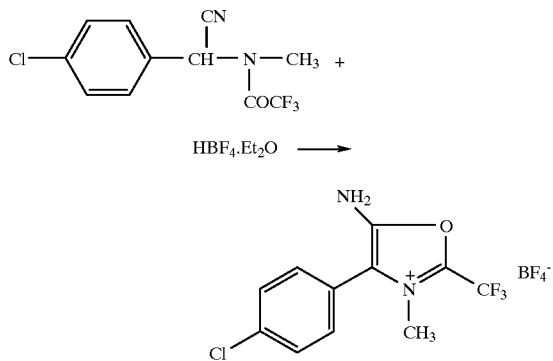

A solution of N-(p-chloro-α-cyanobenzyl-2,2,2-trifluoro-N-methylacetamide (13.8 g, 0.05 mol) in toluene is treated with tetrafluoroboric acid, diethyl etherate (10.5 g as is, 8.9 g real, 0.055 mol) at room temperature. The title oxazolium salt precipitates out as a yellow solid, is filtered, and washed with dry ether and dried under a nitrogen atmosphere. The title product is identified by $^{19}$F NMR analysis (singlet at –60 ppm DMSO-D$_6$)

I claim:
1. A compound of formula I

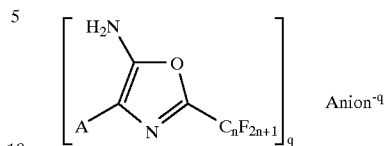

wherein n is an integer of 1, 2, 3, 4, 5, 6, 7, or 8;
q is an integer of 1, 2, or 3;

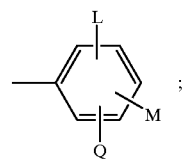

L is hydrogen or halogen;
M and Q are each independently hydrogen, halogen, CN, NO$_2$, C$_1$–C$_4$alkyl, C$_1$–C$_4$haloalkyl, C$_1$–C$_4$alkoxy, C$_1$–C$_4$haloalkoxy, C$_1$–C$_4$alkylthio or when M and Q are on adjacent positions they may be taken together with the carbon atoms to which they are attached to form a ring in which MQ represent the structure —OCH$_2$O—, —OCF$_2$O— or —CH=CH—CH=CH—; and Anion$^{-q}$ is a proton acceptor having a negative q charge selected from the group consisting of bisulfate, sulfate, methanesulfonate, trifluoromethanesulfonate, p-toluenesulfonate, dihydrogen phosphate, hydrogen phosphate, phosphate and tetrafluoroborate; or the tautomers thereof.

2. The compound according to claim 1 wherein q is 1 and the anion is selected from the group consisting of methanesulfonate, trifluoromethanesulfonate, benzenesulfonate, p-toluenesulfonate, naphthalenesulfonate, and tetrafluoroborate.

3. The compound according to claim 1 wherein n is 1 or 2.

4. The compound according to claim 1 wherein L is hydrogen or halogen and M and Q are each independently hydrogen, halogen or C$_1$–C$_4$haloalkyl.

5. The compound according to claim 1:
5-amino-4-(p-chlorophenyl)-2-(trifluoromethyl)oxazole, methanesulfonic acid salt;
5-amino-4-(p-chlorophenyl)-2-(trifluoromethyl)oxazole, p-toluenesulfonic acid salt;
5-amino-4-(3,5-dichlorophenyl)-2-(trifluoromethyl) oxazole, trifluoromethanesulfonic acid salt;
5-amino-4-(3,5-dichlorophenyl)-2-(trifluoromethyl) oxazole, methanesulfonic acid salt;
5-amino-4-[p-(α,α,α,-trifluoro)tolyl]-2-(trifluoromethyl) oxazole, p-toluenesulfonic acid salt;
5-amino-4-(3,4,5-trichlorophenyl)-2-(trifluoromethyl) oxazole, p-toluenesulfonic acid salt;
5-amino-4-[p-(trifluoromethoxy)phenyl]-2-(trifluoromethyl)oxazole, trifluoromethanesulfonic acid salt; or
5-amino-4-[2-(3,4,5-trichloro)thienyl]-2-(trifluoromethyl)oxazole, methanesulfonic acid salt.

6. A compound of formula II

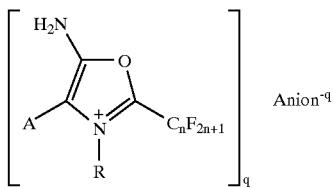
(II)

wherein n is an integer of 1, 2, 3, 4, 5, 6, 7 or 8;
q is an integer of 1, 2, or 3;
R is $C_1$–$C_6$alkyl optionally substituted with one $C_1$–$C_4$alkoxy or phenyl group;
A is

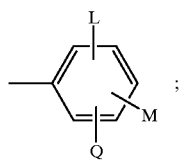
;

L is hydrogen or halogen;
M and Q are each independently hydrogen, halogen, CN, $NO_2$, $C_1$–$C_4$alkyl, $C_1$–$C_4$haloalkyl, $C_1$–$C_4$alkoxy, $C_1$–$C_4$haloalkoxy, $C_1$–$C_4$alkylthio or when M and Q are on adjacent positions they may be taken together with the carbon atoms to which they are attached to form a ring in which MQ represents the structure —$OCH_2O$—, —$OCF_2O$— or —CH=CH—CH=CH—; and
Anion$^{-q}$ is a proton acceptor having a negative q charge selected from the group consisting of bisulfate, sulfate, methanesulfonate, trifluoromethanesulfonate, p-toluenesulfonate, dihydrogen phosphate, hydrogen phosphate, phosphate and tetrafluoroborate; or
the tautomers thereof.

7. The compound according to claim 6 wherein q is 1.

8. The compound according to claim 6 wherein n is 1 or 2.

9. The compound according to claim 6 wherein R is methyl or benzyl.

10. The compound according to claim 6 wherein L is hydrogen or halogen and M and Q are each independently hydrogen, halogen or $C_1$–$C_4$haloalkyl.

11. The compound according to claim 6
5-amino-4-(p-chlorophenyl)-3-methyl-2-(trifluoromethyl)oxazolium tetrafluoroborate;
5-amino-4-(p-bromophenyl)-3-methyl-2-(trifluoromethyl)oxazolium methanesulfonate;
5-amino-4-(3,5-dichlorophenyl)-3-benzyl-2-(trifluoromethyl)oxazolium p-chlorotoluenesulfonate;
5-amino-4-(3,4,5-trichlorophenyl)-3-isopropyl-2-(trifluoromethyl)oxazolium tetrafluoroborate;
5-amino-4-(p-chlorophenyl)-3-methyl-2-(trifluoromethyl)oxazolium bisulfate;
5-amino-4-[( α,α,α-trifluoro)tolyl]-3-benzyl-2-(trifluoromethyl)oxazolium p-chlorotoluenesulfonate;
5-amino-4-[p-(trifluoromethoxy)phenyl]-3-ethyl-2-(trifluoromethyl)oxazolium tetrafluoroborate; or
5-amino-4-[2-(3,4,5-trichloro)thienyl]-2-(trifluoromethyl)oxazolium methanesulfonate.

12. A method for the preparation of a compound of formula I or formula II

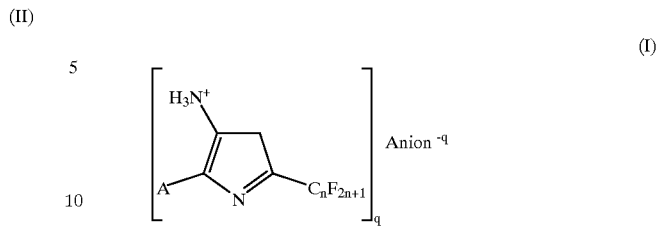
(I)

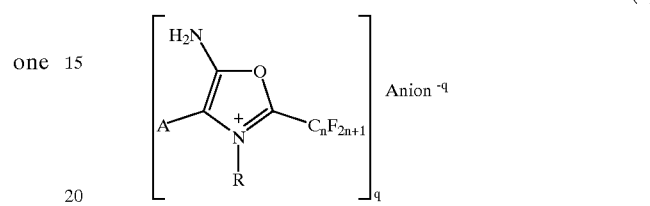
(II)

wherein n is an integer of 1,2,3,4,5,6,7 or 8;
q is an integer of 1, 2,or 3;
R is $C_1$–$C_6$alkyl optionally substituted with one $C_1$–$C_4$alkoxy or phenyl group;

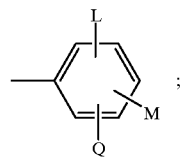
;

L is hydrogen or halogen;
M and Q are each independently hydrogen, halogen, CN, $NO_2$, $C_1$–$C_4$alkyl, $C_1$–$C_4$haloalkoxy, $C_1$–$C_4$alkoxy, $C_1$–$C_4$ haloalkoxy, $C_1$–$C_4$alkylthio or when M and Q are on adjacent positions they may be taken together with the carbon atoms to which they are attached to form a ring in which MQ represents the structure —$OCH_2O$—, —$OCF_2O$— or —CH=CH—CH=CH—; and
Anion$^{-q}$ is a proton acceptor having a negative q charge selected from the group consisting of bisulfate, sulfate, methanesulfonate, trifluoromethanesulfonate, p-toluenesulfonate, dihydrogen phosphate, hydrogen phosphate, phosphate and tetrafluoroborate; or
the tautomers thereof,
which comprises reacting a compound of formula III

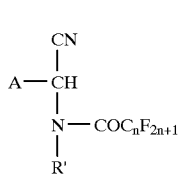
(III)

wherein n and A are as described hereinabove and R' is H or R with at least one molar equivalent of an acid selected from the group consisting of sulfuric acid, methanesulfonic acid, trifluoromethanesulfonic acid, p-toluenesulfonic acid, phosphoric acid, tetrafluoroboric acid and tetrafluoroboric acid complexes in the presence of a solvent and essentially in the absence of water or an acyl halide.

13. The method according to claim 12 wherein the acid is selected from the group consisting of sulfuric acid, methanesulfonic acid, trifluoromethanesulfonic acid, benzenesulfonic acid, p-toluenesulfonic acid, naphthalenesulfonic acid, tetrafluoroboric acid, tetrafluoroboric acid etherate, and tetrafluoroboric acid alkanolate.

14. The method according to claim 13 wherein the solvent is selected from the group consisting of toluene, dimethylformamide, acetonitrile, propionitrile, t-butanol, and mixtures thereof.

* * * * *